United States Patent [19]

Chiu

[11] Patent Number: 5,989,178
[45] Date of Patent: Nov. 23, 1999

[54] MAGNETIC RING

[76] Inventor: Alexander Y. C. Chiu, 122 Flying Mist Isle, Foster City, Calif. 94404

[21] Appl. No.: 08/825,729

[22] Filed: Apr. 2, 1997

[51] Int. Cl.$^6$ ..................................................... A61N 1/00
[52] U.S. Cl. ................................................................ 600/15
[58] Field of Search ............................................. 600/9–15

[56] References Cited

U.S. PATENT DOCUMENTS

| | | | |
|---|---|---|---|
| 3,835,664 | 9/1974 | Nesbit ...................................... | 63/15.6 |
| 4,095,587 | 6/1978 | Ishikawa .................................. | 128/1.3 |
| 4,186,567 | 2/1980 | Monden et al. ......................... | 63/14 R |
| 4,912,944 | 4/1990 | Crosley et al. .......................... | 63/29.2 |
| 5,137,507 | 8/1992 | Park ........................................ | 600/9 |
| 5,139,474 | 8/1992 | Lamond et al .......................... | 600/15 |
| 5,349,725 | 9/1994 | Levy ....................................... | 24/303 |
| 5,720,046 | 2/1998 | Lopez et al. ............................ | 600/15 |

FOREIGN PATENT DOCUMENTS

| | | | |
|---|---|---|---|
| 0650188 | 6/1994 | Australia ................................. | 600/15 |
| 1734777 | 5/1992 | U.S.S.R. ................................. | 600/15 |
| 9504572 | 2/1995 | WIPO ..................................... | 600/9 |

OTHER PUBLICATIONS

Webster's II, New Riverside University Dictionary, 1984.

Primary Examiner—John P. Lacyk
Attorney, Agent, or Firm—Richard L. Miller, P.E.

[57] ABSTRACT

A magnetic ring adapted to be worn on the little finger of the hand. The magnetic ring includes a ring and a pair of permanent magnets that extend from the ring. When the magnetic ring is worn on the little finger of the right hand, the pair of permanent magnets are oriented on the top and bottom, respectively, of the little finger, with the South pole of the magnet that is oriented on the top of the little finger generally contacting the top of the little finger, with the North pole of the magnet that is oriented on the top of the little finger in opposition thereto, with the North pole of the magnet that is oriented on the bottom of the little finger generally contacting the bottom of the little finger, and with the South pole of the magnet that is oriented on the bottom of the little finger in opposition thereto. When the magnetic ring is worn on the little finger of the left hand, the position of the polarities of the pair of permanent magnets are reversed from that of the right hand. The magnetic ring can also be made to fit around all the fingers of the hand and all the toes of the foot.

4 Claims, 3 Drawing Sheets

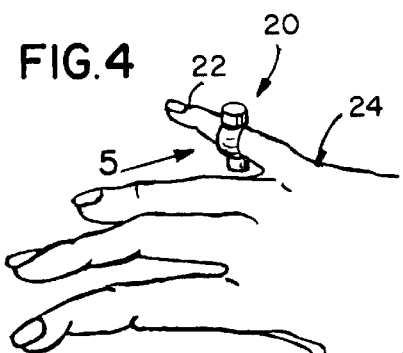
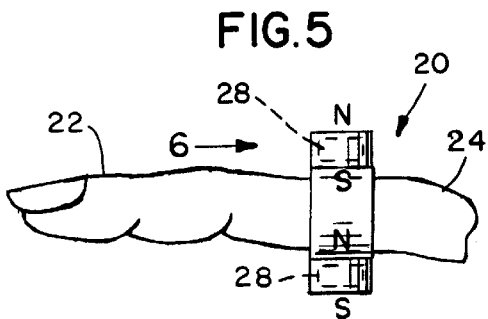
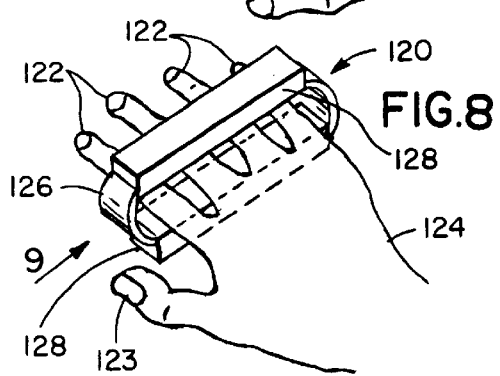
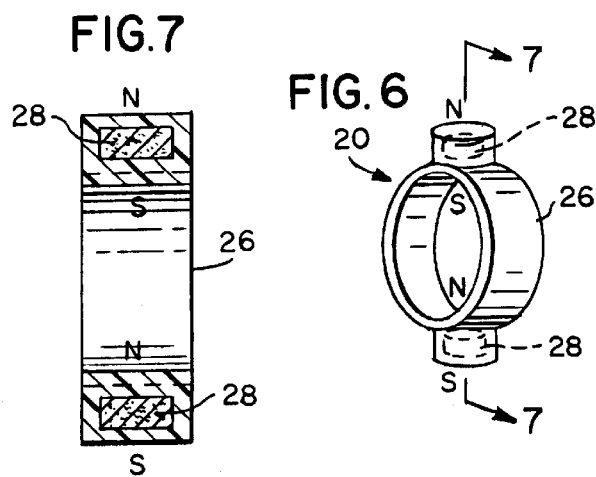
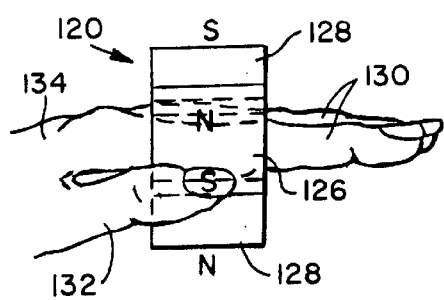
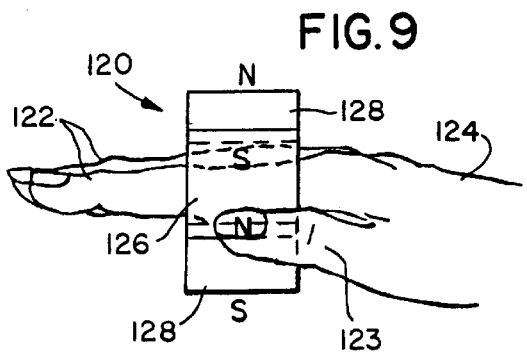

MAGNETIC RING

BACKGROUND OF THE INVENTION

1. Field of the Invention

The present invention relates to a ring. More particularly, the present invention relates to a magnetic ring.

2. Description of the Prior Art

The whole human body is a magnetic community. Each individual cell is a magnet and has polarities of North and South just like a regular magnet. That is why cells attract each other and form finally into a more complicated community, an animal body.

As shown in FIG. 1, a human body carries magnetic flux current which cycles around the body. If this magnetic flux cycle in the body gets stronger, and faster, the healthier the body should become. The reason why a person gets healthier if his magnetic flux becomes stronger or faster is because blood circulation is directly proportional to magnetic flux. The body circulates blood with its natural turbine, magnet flux, which consists of no moving parts but yet still propels blood into a circulating system.

Numerous innovations for magnetic jewelry have been provided in the prior art that will be described. Even though these innovations may be suitable for the specific individual purposes to which they address, however, they differ from the present invention.

FOR EXAMPLE, U.S. Pat. No. 3,835,664 to Nesbit teaches means for reducing the diameter of a finger ring to produce a fit secure and comfortable for the wearer. The ring is fitted with a relatively flat member directly beneath the setting facing inwardly of the ring. This member may be constructed of a magnetic material or may be of a material such as iron which is attracted to a magnet. The member is secured by means of a suitable adhesive or by soldering or the like. In order to reduce the diameter size of the ring, a disc-like shim, which may be a magnet, is positioned on the underside of the secured member. The shim, is not adhesively secured but is secured to the member by magnetic attraction so that if the member is a magnet, the shim need not be, but can be of an attractable material. Shims of varying sizes may be employed so that the diameter of the ring may be modified over considerable reductions.

ANOTHER EXAMPLE, U.S. Pat. No. 4,095,587 to Ishikawa teaches a magnetic ornament, such as a bracelet, a necklace or a chain belt, suitable for promoting good health and personal adornment. The magnetic ornament is comprised of at least one capsule linked with at least one chain. The capsule has enclosed therein one or more pieces of a rare earth-cobalt permanent magnet having the magnetic poles formed on the peripheral surface. At least the surfaces of the capsule and the chain are made of non-magnet corrosion-resistant metal.

STILL ANOTHER EXAMPLE, U.S. Pat. No. 4,186,567 to Monden et al. teaches an ornament adapted to be fixed by permanent magnets and has an ornament piece to which is fixed a gem or the like, and an attracting piece confronting the ornament piece. The ornament piece and/or the attracting piece is provided with a rare earth-cobalt magnet embedded therein, so that these pieces may be held by each other by means of the magnetic attracting force which acts across a non-magnetic body such as an earlobe. The level of the magnetic attracting force is so selected as to fall, when the pieces confront each other across a distance approximately the thickness of an ear lobe, within a range of between 30 grams and 100 grams per square centimeter of attaching area and, at the same time, to be larger than 30 grams per gram of weight of the ornament, so that the user may put on the ornament which may be an earring, without pain nor the fear of unintentional dropping.

YET ANOTHER EXAMPLE, U.S. Pat. No. 4,912,944 to Crosley et al. teaches an article of jewelry comprising a base element which supports an ornamented substrate element thereon by magnetic attraction, both the base element and the substrate element having magnetically attractable properties and at least one of them having the properties of a permanent magnet, whereby the substrate element is interchangeable with other like elements bearing different ornamentation.

FINALLY, STILL YET ANOTHER EXAMPLE, U.S. Pat. No. 5,349,725 to Levy teaches a jewelry closure that includes a magnetic closure and a mechanical closure which is a safety feature, preventing the magnetic closure from being opened inadvertently. A plate-like mechanical closure member attached to one of the magnetic closure members engages a complementarily shaped portion of the other magnetic closure member when the magnetic closure is secured to provide a mechanical second closure for the jewelry. The combined magnetic and mechanical jewelry closure may be used to close chains. The closure may also be disposed on a hinged ring. The ring may be used for passing through ends of a decorative chain as a closure for the chain. The closure may also be used on a hinged ring for wearing on a finger and is particularly useful if the finger joints are swollen. Other uses include adaptation for a hinged charm for closing a chain or for adding to a chain.

It is apparent that numerous innovations for magnetic jewelry have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

The present invention speeds up the blood circulation of the entire body by locating it on the digits of both hands and/or both feet. The present invention speeds up the magnetic flux that is cycled in the body and therefore affects the blood circulation system.

Slow metabolism means that energy and food that are delivered by blood do not reach cells fast enough. Cells are dying faster than they are reproduced as a result of the lacking of energy and food source that is caused by slow blood circulation. With the present invention metabolism is speeded up and allowed to distribute adequate energy and food into entire body cells, keeping the body young and healthy.

The present invention also helps speed up the healing process. Wounds and agonies can heal faster than usual. Old scars can now also reheal and disappear eventually. Why? Because, as mentioned, supra, each single cell in the body is a magnet. If the magnetic flux of the body becomes stronger, cells attract more strongly to each other and therefore create a denser reunion. If cells become denser, the body parts becomes tighter and also stronger.

Shown in FIG. 2 is an example of loose cells which make up weak body tissue. Blood circulation in such a particular body part is also bad.

As shown in FIG. 3, with the use of the present invention, the loose, ununiformed cell group of FIG. 2 are rearranged into a tighter, stronger cell group and therefore generate better blood circulation in that particular area.

ACCORDINGLY, AN OBJECT of the present invention is to provide a magnetic ring that avoids the disadvantages of the prior art.

ANOTHER OBJECT of the present invention is to provide a magnetic ring that is simple and inexpensive to manufacture.

STILL ANOTHER OBJECT of the present invention is to provide a magnetic ring that is simple to use.

BRIEFLY STATED, YET ANOTHER OBJECT of the present invention is to provide a magnetic ring adapted to be worn on the little finger of the hand. The magnetic ring includes a ring and a pair of permanent magnets. The ring is sized to comfortably and snugly fit on the little finger of the hand. The pair of permanent magnets extend from the ring. When the magnetic ring is worn on the little finger of the right hand, the pair of permanent magnets are oriented on the top and bottom, respectively, of the little finger of the right hand, with the South pole of the magnet of the pair of permanent magnets that is oriented on the top of the little finger of the right hand generally contacting the top of the little finger of the right hand, with the North pole of the magnet of the pair of permanent magnets that is oriented on the top of the little finger of the right hand in opposition thereto, with the North pole of the magnet of the pair of permanent magnets that is oriented on the bottom of the little finger of the right hand generally contacting the bottom of the little finger of the right hand, and with the South pole of the magnet of the pair of permanent magnets that is oriented on the bottom of the little finger of the right hand in opposition thereto. When the magnetic ring is worn on the little finger of the left hand, the position of the polarities of the pair of permanent magnets are reversed from that of the right hand. The magnetic ring can also be made to fit around all the fingers of the hand and all the toes of the foot.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures on the drawing are briefly described as follows:

FIG. 4 is a diagrammatic perspective view of the preferred embodiment of the present invention worn on the little finger of the right hand;

FIG. 5 is an enlarged diagrammatic side elevational view taken generally in the direction of arrow 5 in FIG. 4;

FIG. 6 is an enlarged diagrammatic perspective view of the preferred embodiment of the present invention taken generally in the direction of arrow 6 in FIG. 5;

FIG. 7 is an enlarged cross sectional view taken on line 7—7 in FIG. 6;

FIG. 8 is a diagrammatic perspective view of a first alternate embodiment of the present invention worn on all of the fingers of the right hand except the thumb;

FIG. 9 is an enlarged diagrammatic side elevational view taken generally in the direction of arrow 9 in FIG. 8;

FIG. 10 is an enlarged diagrammatic side elevational view of the first alternate embodiment of the present invention worn on all of the fingers of the left hand except the thumb;

Figure 1:
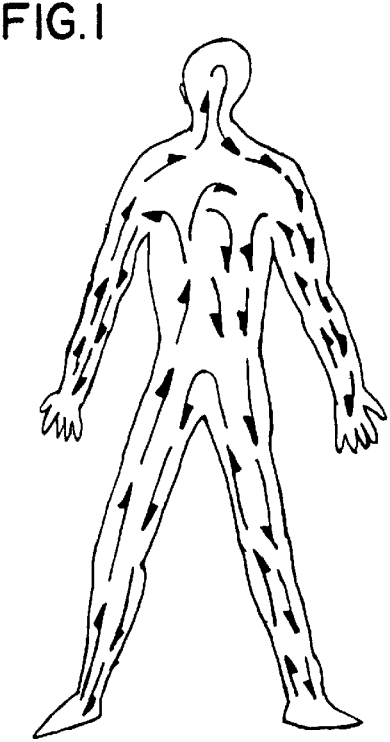
FIG. 1 is a diagrammatic view of the magnet flux current cycle of the human body.
Figure 2:
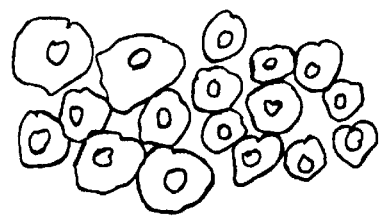
FIG. 2 is a diagrammatic view of loose cells which make up weak body tissue.
Figure 3:
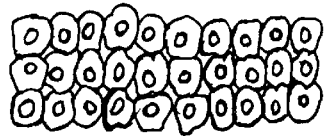
FIG. 3 is a diagrammatic view of the loose cells which make up weak body tissue of FIG. 2 rearranged into a tighter, stronger cell group after utilization of the present invention.
Figure 12:
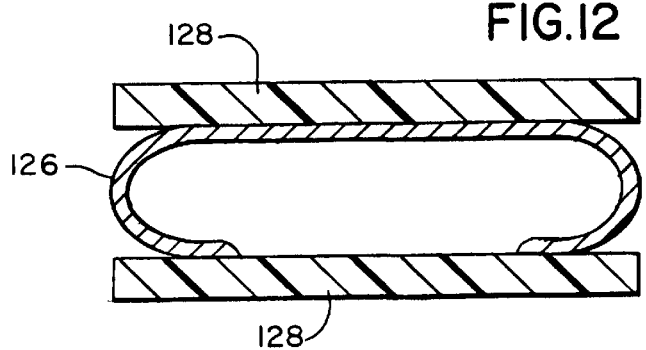
FIG. 12 is an enlarged cross sectional view taken on line 12—12 in FIG. 11.
Figure 11:
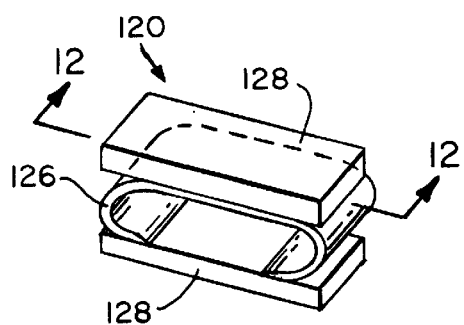
FIG. 11 is a diagrammatic perspective view of the first alternate embodiment of the present invention.

LIST OF REFERENCE NUMERALS UTILIZED
IN THE DRAWING

Preferred Embodiment 20 magnetic ring of the present invention
22 little finger of right hand 24
24 right hand
26 ring
28 pair of permanent magnets First Alternate Embodiment 120 magnetic ring of the present invention
122 all the fingers of right hand 124
123 thumb of right hand 124
124 right hand
126 ring
128 pair of permanent magnets
130 all the fingers of left hand 134
132 thumb of left hand 134
134 left hand Second Alternate Embodiment 220 magnetic ring of the present invention
222 all the fingers of right hand 224
223 thumb of right hand 224
224 right hand
226 ring
228 all the toes of right foot 230
230 right foot Third Alternate Embodiment 320 large magnetic machine Fourth Alternate Embodiment 420 ring shaped magnetic device

DETAILED DESCRIPTION OF THE
PREFERRED EMBODIMENT

Referring now to the figures in which like numerals indicate like parts, and particularly to FIGS. 4 and 5, the preferred embodiment of the magnetic ring of the present invention is shown generally at 20 worn on the little finger 22 of the right hand 24.

The configuration of the preferred embodiment of the magnetic ring 20 can best be seen in FIGS. 6 and 7, and as such will be discussed with reference thereto.

The magnetic ring 20 includes a ring 26 sized to comfortably and snugly fit on the little finger 22 of the right hand 24 and is preferably plastic.

The magnetic ring 20 further includes a pair of permanent magnets 28 that have North poles and South poles, are diametrically opposed, and preferably circular-cylindrically-shaped, are 1 cm in diameter and 0.5 cm in height.

The pair of permanent magnets 28 extend radially outwardly from diametrically opposed positions on the ring 26 and can be encased in the plastic used to form the ring 26 so as to be attached thereto as an integral part thereof.

As shown in FIG. 5, the pair of permanent magnets 28 are oriented on the top and bottom, respectively, of the little finger 22 of the right hand 24 when the magnetic ring 20 is worn on the little finger 22 of the right hand 24, with the South pole of the magnet of the pair of permanent magnets 28 that is oriented on the top of the little finger 22 of the right hand 24 generally contacting the top of the little finger 22 of the right hand 24, with the North pole of the magnet of the pair of permanent magnets 28 that is oriented on the top of the little finger 22 of the right hand 24 in opposition thereto, with the North pole of the magnet of the pair of permanent magnets 28 that is oriented on the bottom of the little finger 22 of the right hand 24 generally contacting the bottom of the little finger 22 of the right hand 24, and with the South pole of the magnet of the pair of permanent magnets 28 that is oriented on the bottom of the little finger 22 of the right hand 24 in opposition thereto.

It is to be understood that when the magnetic ring 20 is worn on the little finger (not shown) of the left hand (not shown) the polarities of the pair of permanent magnets 28 are opposite to that when the magnetic ring 20 is worn on the little finger 22 of the right hand 24 which is of significance since it is preferred that the magnetic ring 20 be worn on both the little finger 22 of the right hand 24 and the little finger (not shown) of the left hand (not shown) simultaneously for best results since the magnetic polarities generate magnetic flux flow which flows through the human body from the magnets on one hand into the magnets placed on the other hand.

Referring now to FIGS. 8 and 9, a first alternate embodiment of the magnetic ring 120 is shown worn on all the fingers 122 except the thumb 123 of the right hand 124.

The configuration of the first alternate embodiment of the magnetic ring 120 can best be seen in FIGS. 8 and 9, and as such will be discussed with reference thereto.

The magnetic ring 120 includes a ring 126 sized to comfortably and snugly fit around all the fingers 122 except the thumb 123 of the right hand 124, and is preferably plastic.

The magnetic ring 120 further includes a pair of permanent magnets 128 that have North poles and South poles, are opposed, parallel, and preferably rectangular-parallelepiped-shaped.

The pair of permanent magnets 128 extend outwardly along opposed positions on the ring 126. The pair of permanent magnets 128 are oriented on the top and bottom, respectively, of all the fingers 122 except the thumb 123 of the right hand 124 when the magnetic ring 120 is worn on all the fingers 122 except the thumb 123 of the right hand 124, with the South pole of the magnet of the pair of permanent magnets 128 that is oriented on the top of all the fingers 122 except the thumb 123 of the right hand 124 generally contacting the top of all the fingers 122 except the thumb 123 of the right hand 124, with the North pole of the magnet of the pair of permanent magnets 128 that is oriented on the top of all the fingers 122 except the thumb 123 of the right hand 124 in opposition thereto, with the North pole of the magnet of the pair of permanent magnets 128 that is oriented on the bottom of all the fingers 122 except the thumb 123 of the right hand 124 generally contacting the bottom of all the fingers 122 except the thumb 123 of the right hand 124, and with the South pole of the magnet of the pair of permanent magnets 128 that is oriented on the bottom of all the fingers 122 except the thumb 123 of the right hand 124 in opposition thereto.

It is to be understood that the pair of permanent magnets 128 can be encased in the plastic used to form the ring 126 so as to be attached thereto as an integral part thereof.

As shown in FIG. 10, it is to be further understood that when the magnetic ring 120 is worn on all the fingers 130 except the thumb 132 of the left hand 134, the polarity of the pair of permanent magnets 128 is opposite to that when the magnetic ring 120 is worn on all the fingers 122 except the thumb 123 of the right hand 124 which is of significance since it is preferred that the magnetic ring 120 be worn on both all the fingers 122 except the thumb 123 of the right hand 124 and all the fingers 130 except the thumb 132 of the left hand 134 simultaneously for best results for the reasons discussed, supra, with reference to the magnetic ring 20.

The configuration of the second alternate embodiment of the magnetic ring 220 can best be seen in FIGS. 13 and 14, and as such will be discussed with reference thereto.

Figure 13:
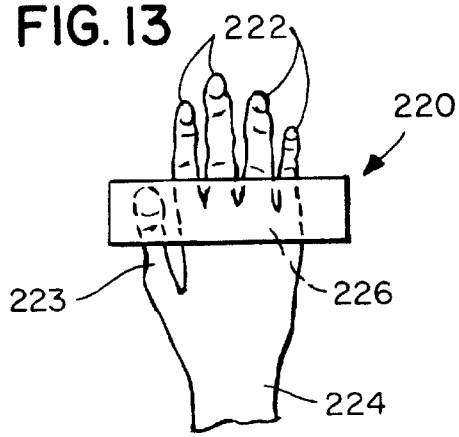
FIG. 13 is a diagrammatic perspective view of a second alternate embodiment of the present invention worn on all of the fingers of the right hand including the thumb.
Figure 14:
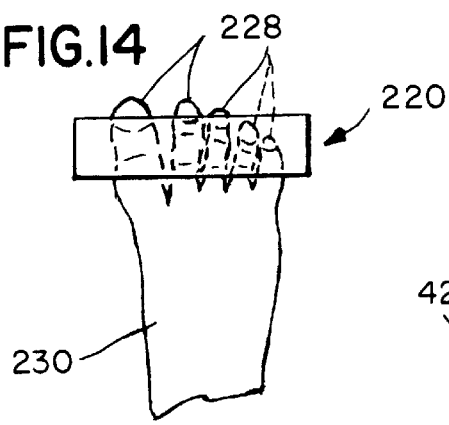
FIG. 14 is a diagrammatic perspective view of the second alternate embodiment of the present invention worn on all of the toes of the right foot including the big toe.

As shown in FIG. 13, the magnetic ring 220 is identical to the magnetic ring 120 except that the ring 226 is sized to comfortably and snugly fit around all the fingers 222 including the thumb 223 of the right hand 224, or as shown in FIG. 14 sized to comfortably and snugly fit around all the toes 228 of the right foot 230.

Figure 15:
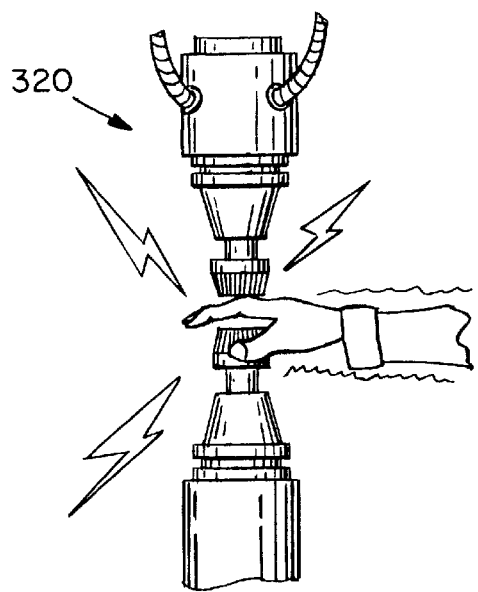
FIG. 15 is a diagrammatic perspective view of a third alternate embodiment of the present invention.

The configuration of a third alternate embodiment of the present invention can best be seen in FIG. 15 and includes a large magnetic machine 320 that supplies the properly positioned polarities.

Figure 16:
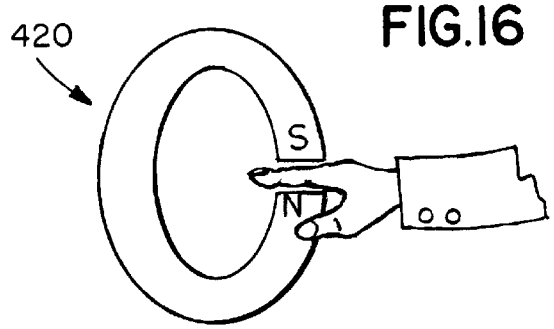
FIG. 16 is a diagrammatic perspective view of a fourth alternate embodiment of the present invention.

The configuration of a fourth alternate embodiment of the present invention can best be seen in FIG. 16 and includes a ring shaped magnetic device 420 that supplies the properly positioned polarities.

It will be understood that each of the elements described above, or two or more together, may also find a useful application in other types of constructions differing from the types described above.

While the invention has been illustrated and described as embodied in a magnetic ring, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A method of utilizing a magnetic ring adapted to be worn on all the fingers including the thumb of each hand to supplement strength and speed of existing magnetic flux current cycled around a human body to increase health of the human body by virtue of blood circulation being directly proportional to magnetic flux and the magnetic flux being a natural turbine to circulate blood and which consists of no moving parts but yet still propels the blood, wherein the magnetic ring has a ring with a size adapted to comfortably and snugly fit on all the fingers including the thumb of each hand and a pair of permanent magnets that extend outwardly along opposed positions on said ring and have North and South poles, said method comprising the steps of:

a) placing a magnetic ring on all the fingers including the thumb of each hand;

b) orientating said South pole of one magnet of said pair of permanent magnets of one said magnetic ring on the top of all the fingers including the thumb of the right hand and said North pole of another magnet of said pair of permanent magnets of said one magnetic ring on the bottom of all the fingers including the thumb of the right hand;

c) contacting generally said South pole of said one magnet of said pair of permanent magnets of said one magnetic ring on the top of all the fingers including the thumb of the right hand and said North pole of said another magnet of said pair of permanent magnets of said one magnetic ring on the bottom of all the fingers including the thumb of the right hand;

d) orientating said North pole of one magnet of said pair of permanent magnets of another said magnetic ring on the top of all the fingers including the thumb of the left hand and said South pole of another magnet of said pair of permanent magnets of said another magnetic ring on the bottom of all the fingers including the thumb of the left hand; and e) contacting generally said North pole of said one magnet of said pair of permanent magnets of said another magnetic ring on the top of all the fingers including the thumb of the left hand and said South pole of said another magnet of said pair of permanent magnets of said another magnetic ring on the bottom of all the fingers including the thumb of the left hand which inherently causes magnetic flux current to flow through the human body from said one magnetic ring on the right hand to said another magnetic ring on the left hand which supplements the strength and the speed of the existing magnetic flux current cycled around the human body to increase the health of the human body by virtue of the blood circulation being directly proportional to the magnetic flux and the magnetic flux being a natural turbine to circulate the blood and which consists of no moving parts but yet still propels the blood.

2. A method of utilizing a magnetic ring adapted to be worn on all the fingers including the thumb of each hand to supplement strength and speed of existing magnetic flux current cycled around a human body to increase health of the human body by virtue of blood circulation being directly proportional to magnetic flux and the magnetic flux being a natural turbine to circulate blood and which consists of no moving parts but yet still propels the blood, wherein the magnetic ring has a ring with a size adapted to comfortably and snugly fit on all the fingers including the thumb of each hand and a pair of permanent magnets that extend outwardly along opposed positions on said ring and have North and South poles, said method comprising the steps of:

a) placing a magnetic ring that is plastic on all the fingers including the thumb of each hand;

b) orientating said South pole of one magnet of said pair of permanent magnets of one said magnetic ring on the top of all the fingers including the thumb of the right hand and said North pole of another magnet of said pair of permanent magnets of said one magnetic ring on the bottom of all the fingers including the thumb of the right hand;

c) contacting generally said South pole of said one magnet of said pair of permanent magnets of said one magnetic ring on the top of all the fingers including the thumb of the right hand and said North pole of said another magnet of said pair of permanent magnets of said one magnetic ring on the bottom of all the fingers including the thumb of the right hand;

d) orientating said North pole of one magnet of said pair of permanent magnets of another said magnetic ring on the top of all the fingers including the thumb of the left hand and said South pole of another magnet of said pair of permanent magnets of said another magnetic ring on the bottom of all the fingers including the thumb of the left hand; and e) contacting generally said North pole of said one magnet of said pair of permanent magnets of said another magnetic ring on the top of all the fingers including the thumb of the left hand and said South pole of said another magnet of said pair of permanent magnets of said another magnetic ring on the bottom of all the fingers including the thumb of the left hand which inherently causes magnetic flux current to flow through the human body from said one magnetic ring on the right hand to said another magnetic ring on the left hand which supplements the strength and the speed of the existing magnetic flux current cycled around the human body to increase the health of the human body by virtue of the blood circulation being directly proportional to the magnetic flux and the magnetic flux being a natural turbine to circulate the blood and which consists of no moving parts but yet still propels the blood.

3. A method of utilizing a magnetic ring adapted to be worn on all the fingers including the thumb of each hand to supplement strength and speed of existing magnetic flux current cycled around a human body to increase health of the human body by virtue of blood circulation being directly proportional to magnetic flux and the magnetic flux being a natural turbine to circulate blood and which consists of no moving parts but yet still propels the blood, wherein the magnetic ring has a ring with a size adapted to comfortably and snugly fit on all the fingers including the thumb of each hand and a pair of permanent magnets that extend outwardly along opposed positions on said ring and have North and South poles and are opposed, parallel, and rectangular-parallelepiped-shaped, said method comprising the steps of:

a) placing a magnetic ring on all the fingers including the thumb of each hand;

b) orientating said South pole of one magnet of said pair of permanent magnets of one said magnetic ring on the top of all the fingers including the thumb of the right hand and said North pole of another magnet of said pair of permanent magnets of said one magnetic ring on the bottom of all the fingers including the thumb of the right hand;

c) contacting generally said South pole of said one magnet of said pair of permanent magnets of said one magnetic ring on the top of all the fingers including the thumb of the right hand and said North pole of said another magnet of said pair of permanent magnets of said one magnetic ring on the bottom of all the fingers including the thumb of the right hand;

d) orientating said North pole of one magnet of said pair of permanent magnets of another said magnetic ring on the top of all the fingers including the thumb of the left hand and said South pole of another magnet of said pair of permanent magnets of said another magnetic ring on the bottom of all the fingers including the thumb of the left hand; and e) contacting generally said North pole of said one magnet of said pair of permanent magnets of said another magnetic ring on the top of all the fingers including the thumb of the left hand and said South pole of said another magnet of said pair of permanent magnets of said another magnetic ring on the bottom of all the fingers including the thumb of the left hand which inherently causes magnetic flux current to flow through the human body from said one magnetic ring on the right hand to said another magnetic ring on the left hand which supplements the strength and the speed of the existing magnetic flux current cycled around the human body to increase the health of the human body by virtue of the blood circulation being directly proportional to the magnetic flux and the magnetic flux being a natural turbine to circulate the blood and which consists of no moving parts but yet still propels the blood.

4. A method of utilizing a magnetic ring adapted to be worn on all the fingers including the thumb of each hand to supplement strength and speed of existing magnetic flux current cycled around a human body to increase health of the human body by virtue of blood circulation being directly proportional to magnetic flux and the magnetic flux being a natural turbine to circulate blood and which consists of no moving parts but yet still propels the blood, wherein the magnetic ring has a ring with a size adapted to comfortably and snugly fit on all the fingers including the thumb of each hand and a pair of permanent magnets that extend outwardly along opposed positions on said ring and have North and South poles and are encased in said ring so as to be attached thereto as an integral part thereof, said method comprising the steps of:

a) placing a magnetic ring on all the fingers including the thumb of each hand;

b) orientating said South pole of one magnet of said pair of permanent magnets of one said magnetic ring on the top of all the fingers including the thumb of the right hand and said North pole of another magnet of said pair of permanent magnets of said one magnetic ring on the bottom of all the fingers including the thumb of the right hand;

c) contacting generally said South pole of said one magnet of said pair of permanent magnets of said one magnetic ring on the top of all the fingers including the thumb of the right hand and said North pole of said another magnet of said pair of permanent magnets of said one magnetic ring on the bottom of all the fingers including the thumb of the right hand;

d) orientating said North pole of one magnet of said pair of permanent magnets of another said magnetic ring on the top of all the fingers including the thumb of the left hand and said South pole of another magnet of said pair of permanent magnets of said another magnetic ring on the bottom of all the fingers including the thumb of the left hand; and e) contacting generally said North pole of said one magnet of said pair of permanent magnets of said another magnetic ring on the top of all the fingers including the thumb of the left hand and said South pole of said another magnet of said pair of permanent magnets of said another magnetic ring on the bottom of all the fingers including the thumb of the left hand which inherently causes magnetic flux current to flow through the human body from said one magnetic ring on the right hand to said another magnetic ring on the left hand which supplements the strength and the speed of the existing magnetic flux current cycled around the human body to increase the health of the human body by virtue of the blood circulation being directly proportional to the magnetic flux and the magnetic flux being a natural turbine to circulate the blood and which consists of no moving parts but yet still propels the blood.

\* \* \* \* \*